US008815303B2

(12) United States Patent
Lewis

(10) Patent No.: US 8,815,303 B2
(45) Date of Patent: Aug. 26, 2014

(54) MULTIFUNCTIONAL COMPOSITIONS HAVING COMBINED INSECTICIDAL, MITICIDAL AND FUNGICIDAL ACTIVITY

(76) Inventor: Susan E. Lewis, Cambria, CA (US)

(*) Notice: Subject to any disclaimer, the term of this patent is extended or adjusted under 35 U.S.C. 154(b) by 66 days.

(21) Appl. No.: 13/089,175

(22) Filed: Apr. 18, 2011

(65) Prior Publication Data

US 2011/0195134 A1 Aug. 11, 2011

Related U.S. Application Data

(62) Division of application No. 12/869,500, filed on Aug. 26, 2010, which is a division of application No. 11/176,967, filed on Jul. 6, 2005, now abandoned.

(60) Provisional application No. 60/586,485, filed on Jul. 6, 2004, provisional application No. 60/603,293, filed on Aug. 19, 2004.

(51) Int. Cl.
*A01N 59/00* (2006.01)
*A01N 37/02* (2006.01)
*A01P 7/04* (2006.01)
*A01N 65/00* (2009.01)

(52) U.S. Cl.
CPC .............. *A01N 37/02* (2013.01); *A01N 65/00* (2013.01)
USPC ........................... 424/717; 514/558; 514/560

(58) Field of Classification Search
CPC ... A01N 37/02; A01N 65/00; A01N 2300/00; A01N 31/02; A01N 59/04; A01N 37/06; A01N 37/12
USPC ................... 424/717; 514/558, 560
See application file for complete search history.

(56) References Cited

U.S. PATENT DOCUMENTS

| | | | |
|---|---|---|---|
| 2,087,028 | A | 7/1937 | Gnadinger |
| 5,123,950 | A | 6/1992 | Homma et al. |
| 5,518,987 | A | 5/1996 | Winston |
| 5,739,172 | A * | 4/1998 | Jones ........................ 424/70.22 |
| 5,891,466 | A | 4/1999 | Yesair |
| 6,231,865 | B1 | 5/2001 | Hsu et al. |
| 6,548,085 | B1 | 4/2003 | Zobitne et al. |
| 7,393,528 | B2 * | 7/2008 | Tvedten ..................... 424/94.63 |
| 2001/0014315 | A1 | 8/2001 | Harbeck |
| 2002/0173436 | A1 * | 11/2002 | Sonnenberg et al. ......... 510/141 |
| 2004/0229801 | A1 * | 11/2004 | Kawabe et al. ................ 514/12 |
| 2005/0244445 | A1 | 11/2005 | Anderson |

FOREIGN PATENT DOCUMENTS

| | | |
|---|---|---|
| WO | WO-0180820 | 11/2001 |
| WO | WO-0191555 | 12/2001 |
| WO | WO-2006055029 | 5/2006 |

OTHER PUBLICATIONS

"Bite Blocker All Natural, 'Deet Free' Insect Repellent" retrieved from http://www.drugstore.com/products/prod.asp?pid=155091 &catid=47206&brand=47637&tr on Jul. 29, 2009, 2 pages.
Bite Blocker TM (Herbal Insect Repellent Spray and Herbal Lotion) [online], last updated Jun. 6, 2004 [retrieved May 23, 2009], Retrieved from the Internet<http://web.archive.org/web/*/http://www.biconet.com/personal/biteblocker.html>.
Database CA [Online}, Chemical Abstracts Service, Columbus, Ohio, US; Quesada, Jorge Martinez: "Antifungal soap for skin topical treatment," XP002462854, retrieved from STN, Database accession No. 2006:68060, & BR 2 004 724 A (ALC-Alergia Clinica Laborator.
Database CA [Online}, Chemical Abstracts Service, Columbus, Ohio, US; Shin, Chung Sun: "Antibacterial soap containing essential oil extracted from pine needles and preparation method thereof," XP002462853, retrieved from STN, Database accession No. 2006:67.
Database CA, Chemical Abstracts Service, Columbus, Ohio, US;XP002462855, retrieved from STN-International, Database accession No. XP002462855, retrieved from STN-International, Database accession No. 1913:18101, & CA 147 500 A (Ellis C.), Apr. 22, 1913, abstract.
Database WPI Week 200559, Derwent Publications Ltd., London, GB; An 2005-579566, XP002462857, & KR 2005 030 497 A (Cast Co Ltd), Mar. 30, 2005. abstract.
Kiwi Vision (Frequently Asked Questions About Handmade Soap) [online], Aug. 16, 2004 [retrieved Oct. 10, 2008], Retrieved from the Internet<http://web.archive.org/web/20040416101937/http://kiwivision.com/faq/>.
Hood, et al., "Effect of essential oil concentration on the pH of nutrient and Iso-sensitest broth", *Phytother Res.* Nov. 2004;18(11):947-9.
Horst, et al., "Managing Diseases of Ornamentals with Bicarbonates and Determining their Mode of Action", *Progress Report to the American Floral Endowment,* Aug. 21, 1992 (4 pages).
Thomas, et al., "Journal of the American Pomological Society", Jan. 1, 2004, abstract.
Browning; *300 Handcrafted Soaps: Great Melt & Pour Projects;* 2003, Sterling Publishing Company, pp. 1-144.
Hopkins; *The Scientific American Cyclopedia of Formulas;* 1913, Munn & Co., pp. 1-1097.

(Continued)

Primary Examiner — Janet Epps-Smith
Assistant Examiner — Courtney Brown
(74) *Attorney, Agent, or Firm* — Thomas D. Wilhelm; Wilhelm Law, S.C.

(57) ABSTRACT

Particular aspects provide novel insecticide/miticide/fungicide compositions, and methods for using same for safe, environmentally friendly control of insects, mites and fungal pests in, e.g., gardening and commercial growing. Preferably, the compositions comprise organic or pure ingredients. Particular embodiments comprise: a fatty acid soap base (e.g., saponified soap with retained glycerin; or fatty acid salts with glycerin); at least one essential oil; an optional food oil; and a bicarbonate reagent, along with water. Additional embodiments comprise: a soap base, and/or glycerin or other suitable base; at least one organic or pure plant essential oil; an organic or pure food oil; and a bicarbonate reagent, along with water as diluent and carrier, and methods for using same. Further aspects provide a method for controlling mite and fungal pests with a single composition comprising, along with an aqueous carrier or diluent: a non-petroleum-based food oil; and a bicarbonate agent.

21 Claims, No Drawings

(56) References Cited

OTHER PUBLICATIONS

Non-Final Office Action from U.S. Appl. No. 12/869,500 mailed Oct. 19, 2010.

U.S. Appl. No. 11/176,967, filed Jul. 6, 2005.
U.S. Appl. No. 12/869,500, filed Aug. 26, 2010.
U.S. Appl. No. 60/586,485, filed Jul. 6, 2004.
U.S. Appl. No. 60/603,293, filed Aug. 19, 2004.

* cited by examiner

MULTIFUNCTIONAL COMPOSITIONS HAVING COMBINED INSECTICIDAL, MITICIDAL AND FUNGICIDAL ACTIVITY

CROSS-REFERENCE TO RELATED APPLICATIONS

The present application is a divisional of U.S. patent application Ser. No. 12/869,500, filed 26 Aug. 2010, which is incorporated by reference herein in its entirety, and which is a divisional of U.S. patent application Ser. No. 11/176,967, filed 6 Jul. 2005, which is incorporated by reference herein in its entirety, and which claims the benefit of priority to U.S. Provisional Patent Application Nos.: 60/586,485, filed 6 Jul. 2004; and 60/603,293, filed 19 Aug. 2004; both of which are incorporated by reference herein in their entirety.

FIELD OF THE INVENTION

Aspects of the present invention relate generally to novel multi-functional compositions and methods for using same, and more particularly to novel compositions and organic compositions that have combined insecticidal, miticidal and fungicidal activities.

BACKGROUND

Insecticidal soaps are known in the art, typically comprising potassium salts of fatty acids, along with ethyl alcohol. However, such prior art products are often ineffective, can be generally damaging to horticulture (e.g., vegetables, fruits, berries and ornamentals), and have multiple additional disadvantages. For example, some conventional insecticidal soaps, although listed for use in organic gardening or farming (OMRI listing, etc.), actually contain non-organic ingredients rendering them unsuitable for many uses, not only for commercial growing, but also by many organic growers where environmentally-friendly insect control is needed in the context of individual gardening and use by minors (e.g., children, adolescents). Additionally, and significantly, such prior art products have been narrowly or specifically developed for use as insecticides, and thus gardeners and growers must purchase and apply multiple separate products to address the three common and most critical growing concerns; namely, insects, mites and fungal diseases.

For example, U.S. Pat. No. 6,548,085 to Zobitne et al. teaches insecticidal compositions comprising, as active ingredients: an essential oil; and sodium lauryl sulfate (SLS) in synergistic proportions. However, while Zobitne et al. teach that the Environmental Protection Agency (which regulates the use of potentially toxic ingredients in pesticidal compositions under the Federal Insecticide, Fungicide and Rodenticide Act) has deregulated the use of SLS, SLS is nonetheless known in the art to have degenerative effects on cell membranes, is known to induce corneal damage in rabbit eyes under some circumstances, and is used around the world in clinical studies as a significant skin irritant. SLS is prepared by sulfation of lauryl alcohol with either sulfur tiroxide or chlorosulfonic acid, followed by neutralization with sodium hydroxide. Carcinogenic nitrates can form in the manufacturing of SLS or by its interaction with other nitrogen bearing ingredients within a formulation utilizing this ingredient (see, e.g., Final Report on the Safety Assessment of Sodium Lauryl Sulfate, *J. Amer. Cole of Toxicology*, vol. 2, number 7, 1983). Moreover, other studies have indicated that SLS enters and maintains residual levels in the heart, liver, lungs, and brain from skin contact, and other research has indicated that SLS may damage the immune system, particularly in the skin (id.). Likewise, U.S. Pat. No. 6,231,865 to Hsu et al. teaches pesticidal compositions comprising garlic oil, along with either cottonseed oil or cinnamon oil, and additionally including 10% SLS as an emulsifier.

Additionally, SLS is known in the art to be harsh on plants, as are shorter-chain fatty acids having 9 carbon atom chains or less, which actually have herbicidal properties.

There is a pronounced need in the art for safe, environmentally friendly, reliable and robust methods and synergistic compositions that can be used for effective treating, controlling and/or preventing insects, mites and fungal diseases.

SUMMARY OF THE INVENTION

Aspects of the present invention provide novel safe, environmentally friendly, reliable and robust methods and compositions having substantial utility for treating, controlling and/or preventing insects, mites and fungal diseases. The inventive multi-functional compositions comprise ingredients that act synergistically to provide for effective treating, controlling and/or preventing insects, mites and fungal diseases through application of a single composition.

The inventive compositions and ingredients are combined in a way that optimizes the insecticidal, miticidal or fungicidal properties of each. Particular aspects provide an organic or pure insecticide/miticide/fungicide that overcomes the shortcomings of the prior art, to provide an effective alternative to existing products which contain harmful chemicals, or ineffective and/or harmful ingredients carried, for example, in ethyl alcohol in such percentages of total product content as to render them ineffective.

Existing products, even those that appear as approved for organic growing by certain rating organizations (OMRI), contain non-organic/synthetic ingredients, or ingredients that are combined with less-than-desirable carriers (such as ethyl alcohol) that make them a less-than-ideal choice for organic growers. Preferred aspects of the present invention comprise only organic or pure and/or food/pharmaceutical grade ingredients, or those food oil ingredients indicated as exempt from EPA registration by virtue of their appearance on the FIFRA 25(b) list or Class 4(a) list making it completely safe for use by organic growers. Preferably, the inventive compositions are packaged in a Certified Organic facility under strict USDA rules and regulations.

Particular aspects address the concerns of gardeners, growers and government officials in many or most states and federal agencies relating to the continued use of conventional chemicals as insecticides both for the known harmful (and potentially deadly as in the case of carcinogenic chemicals) effects to humans incurred in the process of application, as well as the larger threat of harm to humans, animals and plant life in general, by virtue of the presence of harmful (and potentially deadly) chemicals in the water supply and in the soils of millions of acres of agricultural production land.

Particular preferred aspects provide an organic or pure insecticide/miticide/fungicide that combines the insect repelling or killing properties of individual insecticides, fungicides and miticides into a single product having equivalent or greater repelling, killing properties, miticidal properties and fungal knock-down than exists in current products. Individual gardeners, minor use and commercial growers presently purchase multiple products for pest and fungal disease control, and the management of pests and fungal disease becomes, therefore, costly and time-consuming. Particular aspects achieve greater efficiency by combining pesticidally, miticidally and fungicidally effective ingredients in a single product, and achieve greater cost and time effectiveness as a result.

Particular aspects provide methods for controlling insect, mite and fungal pests with a single composition, comprising contacting at least one pest, or a surface or plant or portion thereof susceptible to the at least one pest, with a pesticidally effective amount of a composition comprising, along with an aqueous carrier or diluent: a fatty acid soap base; and an essential oil, wherein controlling insect, mite and fungal pests with a single composition is afforded. In particular aspects, the fatty acid soap base comprises at least one saponified oil with retained glycerin. In alternate aspects, the fatty acid soap base comprises at least one fatty acid salt, along with glycerin. Preferably, the soap base is present at about 0.01% to about 40% by volume, at about 5% to about 20% by volume, or at about 10% to about 15% by volume. Preferably, the essential oil is present at about 0.01% to about 40% by volume, at about 5% to about 10% by volume, or at about 1% to about 10% by volume. In additional aspects, the composition further comprises about 0.01% to about 5% by volume, or about 2.0% by volume of exogenous glycerin. In yet further aspects, the composition further comprises a fungicidal agent (e.g., bicarbonate agent, sulfur agent, copper agent, etc.). Preferably, the bicarbonate agent comprises potassium bicarbonate present at about 0.02% to about 3% by weight, or at about 0.02% to about 2.0% by weight. Preferably, the saponified oil is a saponified plant oil. In particular aspects, the fatty acid soap base is present at about 1% to about 15% by weight, the essential oil is present at about 0.01% to about 5% by weight, a food oil is present at about 1% to about 10% by weight, and the bicarbonate agent comprises a bicarbonate salt present at about 0.02% to about 2.0% by weight. In particular embodiments, the essential oil and the food oil are different oils, each present in the composition at about 0.1% to about 10% by weight, or at about 1% to about 10% by weight. Preferably, the essential oil comprises at least one of peppermint and rosemary, the food oil comprises at least one of cottonseed, soybean, and canola, and the bicarbonate agent comprises potassium bicarbonate at about 2% by weight. Preferably, the bicarbonate agent comprises at least one selected from the group consisting of sodium bicarbonate, potassium bicarbonate and ammonium bicarbonate. Preferably, the soap base and the essential oil are all organic. Contacting comprises contacting once or on a plurality of occasions. Additional aspects provide compositions for controlling insect, mite and fungal pests, having the above-described compositions and variations.

Further aspects provide methods for controlling insect, mite and fungal pests with a single composition, comprising contacting at least one pest, or a surface or plant or portion thereof susceptible to the at least one pest, with a pesticidally effective amount of a composition comprising, along with an aqueous carrier or diluent: a fatty acid soap base; an essential oil; and a fungicidal reagent (e.g., bicarbonate reagent, sulfur reagent, copper reagent, etc.), wherein controlling insect, mite and fungal pests with a single composition is afforded. In particular aspects, the fatty acid soap base comprises at least one saponified oil with retained glycerin. In alternate aspects, the fatty acid soap base comprises at least one fatty acid salt, along with glycerin. Preferably, the fatty acid salts comprise oleic acid. In particular aspects the soap base is present at about 0.01% to about 40% by volume, at about 5% to about 20% by volume, or at about 10% to about 15% by volume. In particular aspects the essential oil is present at about 0.01% to about 40% by volume, at about 5% to about 10% by volume, or at about 1% to about 10% by volume. In additional aspects, the compositions comprise about 0.01% to about 5% by volume, or about 2.0% by volume of exogenous glycerin. Preferably, the bicarbonate reagent comprises potassium bicarbonate present at about 0.02% to about 3% by weight, or at about 0.02% to about 2.0% by weight. In particular aspects, the soap base is present at about 1% to about 15% by weight, the essential oil is present at about 0.01% to about 5% by weight, a food oil is present at about 1% to about 10% by weight, and the bicarbonate agent comprises a bicarbonate salt present at about 0.02% to about 2.0% by weight. In particular aspects, the essential oil and the food oil are different oils, each present in the composition at about 0.1% to about 10% by weight, or at about 1% to about 10% by weight. Preferably, the essential oil comprises at least one of peppermint and rosemary, the food oil comprises at least one of cottonseed, soybean and canola, and the bicarbonate agent comprises potassium bicarbonate at about 2% by weight. Preferably, the bicarbonate agent comprises at least one selected from the group consisting of sodium bicarbonate, potassium bicarbonate and ammonium bicarbonate. Preferably, the soap base and the essential oil are all organic. Contacting comprises contacting once or on a plurality of occasions. In further embodiments, the composition further comprises an amount of Vitamin E sufficient to act as a stabilizer. Additional aspects provide compositions for controlling insect, mite and fungal pests, having the above-described compositions and variations.

Yet additional aspects provide methods for controlling mite and fungal pests with a single composition, comprising contacting at least one pest, or a surface or plant or portion thereof susceptible to the at least one pest, with a pesticidally effective amount of a composition comprising, along with an aqueous carrier or diluent: a non-petroleum-based food oil; and a fungicidal agent (e.g., bicarbonate reagent, sulfur reagent, copper reagent), wherein controlling mite and fungal pests with a single composition is afforded. In particular embodiments, the non-petroleum-based food oil is present at about 0.01% to about 40% by volume, at about 5% to about 10% by volume, or at about 1% to about 10% by volume. In particular aspects, the composition further comprises about 0.01% to about 5% by volume, or about 2.0% by volume of exogenous glycerin. Preferably, the bicarbonate agent comprises potassium bicarbonate present at about 0.02% to about 3% by weight, or at about 0.02% to about 2.0% by weight. In particular embodiments, the non-petroleum-based food oil is present at about 0.01% to about 20% by weight, or at about 0.1% to about 10% by weight, and the bicarbonate agent comprises a bicarbonate salt present at about 0.02% to about 5.0% by weight, or at about 0.02% to about 2% by weight. Preferably, the non-petroleum based food oil is at least one selected from the group consisting of soybean, cottonseed and canola. Preferably, the non-petroleum based food oil is organic. Additional aspects provide compositions for controlling insect, mite and fungal pests, having the above-described compositions and variations.

BRIEF DESCRIPTION OF THE DRAWINGS

There are no figures or drawings, the present specification providing ample and sufficient written description and enabling support for the novel and surprisingly effective inventive compositions and methods for using same described, disclosed and claimed herein.

DETAILED DESCRIPTION OF THE INVENTION

Definitions

The term "organic" as used herein refers to those compounds and compositions that are derived from a natural source. Preferably, the natural source is a plant source.

The term "pest" as used herein is meant to refer to those pests and parasites commonly encountered in individual and commercial gardening a plant growing, and minimally includes insects (e.g., thrips, aphids, scales, whiteflies, leafhoppers, earwigs, mealybugs, ants, cucumber beetles, etc.), mites (e.g., two spotted spider mites, red spider mites, etc.) and fungus (e.g., powdery mildew, downey mildew, blackspot, rusts, *Rhizoctonia* sp., *Trichoderma* sp., and *Botrytis* sp., etc.).

The term "pesticidally effective amount" as used herein refers to an amount of an inventive composition sufficient for controlling (as defined herein below) at least one plant parasite. In specific aspects, the at least one plant parasite is at least one selected from the group consisting of insects, mites and fungus, and a parasiticidally effective amount refers to at least one of a insecticidally, miticidally, and fungicidally effective amount.

The term "controlling" in the context of plant pests (e.g., insects, mites and fungus) as used herein, refers to any one of treating, killing, controlling, preventing, repelling, mitigating or any combination thereof, and wherein these terms are intended to broadly encompass repelling, reduction in severity, alleviating or reducing in addition to killing, elimination, substantial elimination, prevention and substantial prevention.

The term "essential oil" as used herein refers generally to plant oils (e.g., from the flowers, fruits, leaves, roots, seeds, and bark), and some animal oils (e.g., fish oils) including those having an aromatic essence. Essential oils include, but are not limited to volatile liquids that are mostly water insoluble but freely soluble in alcohol, ether, and vegetable and mineral oils. Essential oils include, but are not limited to peppermint oil, cedar oil, castor oil, clove oil, geranium oil, lemongrass oil, linseed oil, mint oil, thyme oil, rosemary oil, cornmint oil (*Mentha arvensis*), garlic oil, anise oil, basil oil, camphor oil, citronella oil, eucalyptus oil, fennel oil, ginger oil, grapefruit oil, lemon oil, lime oil, mandarin oil, orange oil, pine needle oil, pepper oil, rose oil, tangerine oil, tea tree oil, tee seed oil, mineral oil and fish oil. Essential oils also include "food oils" commonly collected for consumption by humans, including, but not limited to corn, olive, canola, cottonseed, cinnamon, almond, coconut, hemp, soybean, sesame, pumpkin, jojoba, oregano, tea, etc. Essential oils are typically obtained, for example, by one or more methods including: steam distillation; extraction by volatile solvents; expression by hand or machine; and enfleurage (wherein fat is used as a solvent). Essential oils, synthesized or obtained from natural sources by any one of the above methods, are often purified by vacuum distillation. Essential oils may also be synthetically produced, and such essential oils are encompassed within the scope of the present invention.

The term "bicarbonate agent" as used herein refers to a bicarbonate salt (e.g., sodium bicarbonate, potassium bicarbonate, ammonium bicarbonate, etc.), and to solutions thereof.

The term "saponification" as used herein refers to the art recognized process of soap making involving reaction of plant oils (e.g., coconut, palm, olive, hemp, etc.) or animal fats with strong alkali (e.g., potassium hydroxide or sodium hydroxide) to produce soap and glycerin.

The term "retained glycerin" as used herein refers to the glycerin generated during saponification (e.g., of an oil or fat), to produce a soap, and wherein the glycerin is retained with the saponified soap preparation.

The term "exogenous glycerin" as used herein refers to extra glycerin that is added to particular inventive compositions, in addition to the retained glycerin (as defined herein) already present by virtue of saponification.

The term "carrier" as used herein means an inert or fluid material (e.g., water), which may be pure or organic and of natural origin, with which the active compounds are mixed or formulated to facilitate its application to the plants/crops to be treated.

I. Novel Methods and Compositions for Controlling Multiple Types of Plant Parasites with a Single Composition Particular aspects of the present invention provide novel multifunctional compositions having substantial utility for controlling, with one or more applications of a single composition, multiple types of parasites (e.g., insects, mites and fungus). Particular embodiments provide "organic" or "pure" multi-functional compositions useful, for example, as an insecticide, miticide and/or fungicide, with application of a single composition.

In particular aspects, the inventive compositions comprise: a soap base; at least one essential oil; a bicarbonate reagent, (e.g., USP potassium bicarbonate, or sodium bicarbonate or any other bicarbonate having utility for the present purposes); and water as diluent and/or carrier. In preferred embodiments, the soap base and essential oil(s) are "organic" or "pure." In particular aspects, the components are blended and bottled by a certified organic food manufacturer under strict quality control. For example, the ingredients are blended in stainless steel tanks under the standards and guidelines of the USDA for Organic products.

Soaps. Particular compositions comprise a soap base, which comprises at least one saponified organic oil (e.g., coconut oil, olive oil, hemp oil, jojoba oil, mentha armensis, etc.) with retained glycerin. In particular aspects, the soap base is present in the inventive compositions at about 0.01% to about 40% by volume, at about 0.01% to about 30% by volume, at about 5% to about 25% by volume, at about 10% to about 20% by volume, at about 10% to about 25% by volume, at about 5% to about 20% by weight, or at about 10% to about 15% by weight. The soap base is the result of a saponification reaction between oils or animal fats (e.g., certified organic) of, for example, coconut, palm, olive or hemp, which are reacted with strong alkali (e.g., potassium hydroxide or sodium hydroxide). This art-recognized process is an acid-base hydrolysis reaction involving hydrolysis of fatty acid glycerides (esters) to produce fatty acid salts (e.g., soap) and glycerin. The net result of the process is soap, glycerin and water with no waste products. The reaction conditions are typically under heat and pressures (e.g., at about 260 degrees F. and 15 psi, respectively).

Exogenous glycerin. Particular compositions comprise, in addition to a soap base and retained glycerin, about 0.01% to about 5% of exogenous glycerin. Preferably, exogenous glycerin is present in the compositions at about 0.5% to about 3%. Preferably, exogenous glycerin is present in the compositions at about 2.0%. According to aspects of the present invention, glycerin synergizes with other ingredients to enhance one or more pesticidal activities, and to provide for a better appearance on plant parts (e.g., for shiny leaves). Without being bound by mechanism, the glycerin serves to preclude deposition of, for example, fatty acid salts and/or bicarbonate salts (see below describing bicarbonate-containing embodiments). Fatty acid salts of prior art products can form deposits on plants, causing leaf burn and leaf fall (particularly over extended application periods), and may result in plant death. The present invention thus solves this art-recognized problem by providing glycerin, which serves to eliminate chalky residue, thereby eliminating leaf burn and leaf fall. Furthermore, glycerin absorbs the essential oil and traps its repellent properties to provide for extended protection from new infestations for several (e.g., up to four weeks) weeks, depending upon the conditions, thus further reducing pesticide use in the environment.

Essential oils. Particular compositions comprise, in addition to a soap base, one or more organic essential oils that are added to the soap base for their pesticidal properties. In particular aspects, the soap base may also contain at least one of sea salt, citric acid, or vitamin E (e.g., tocopherols) for stability. There are numerous variations of the inventive soap-based compositions, dependent upon the amount of diluent, colorants and/or essential oils used during the mixing process. In preferred aspects, the soap base and mixtures thereof are liquids, and the variations are preferably limited to retain or substantially retain the soap's liquid properties (turning the soap into solid or bar form would require the addition of numerous other ingredients, and is not preferred). Representative organic or pure essential oils include, but are not limited to, peppermint oil, lavender oil, cedar oil, castor oil, clove oil, geranium oil, lemongrass oil, linseed oil, mint oil, thyme oil, rosemary oil, cornmint oil (*Mentha arvensis*), garlic oil, anise oil, basil oil, camphor oil, citronella oil, eucalyptus oil, fennel oil, ginger oil, grapefruit oil, lemon oil, lime oil, mandarin oil, orange oil, pine needle oil, pepper oil, rose oil, tangerine oil, tea tree oil, tee seed oil, mineral oil and fish oil. Peppermint oil is an exemplary preferred essential oil. Essential oils also include "food oils" commonly collected for consumption by humans, including, but not limited to corn, olive, canola, cottonseed, cinnamon, almond, coconut, hemp, soybean, sesame, pumpkin, jojoba, oregano, tea, etc. Soybean oil is an exemplary preferred food oil. The essential oils may, for example, be expeller pressed, retrieved by steam distillation or mechanical extraction. Plant essences may be extracted mechanically or through steam distillation of the leaves, stems, flowers and other parts of the plant. Variations may include differences in viscosity or color dependent upon the method of extraction, and the conditions under which the oils were processed (with heat), as well as the origin of the plants, grains or seeds from which the oils are extracted. In particular aspects, one or more organic or pure essential oils is present in the inventive compositions at about 0.01% to about 40% by volume, at about 0.01% to about 30% by volume, at about 5% to about 25% by volume, at about 10% to about 20% by volume, at about 10% to about 25% by volume, at about 5% to about 20% by weight, or at about 5% to about 10% by weight, depending on formulation, application and dilution.

Bicarbonate reagent. Particular compositions comprise a bicarbonate reagent (e.g., USP potassium bicarbonate or sodium bicarbonate or any other bicarbonate having utility for the present purposes), in addition to a soap base, and/or one or more organic essential oils as discussed above. In particular aspects, a bicarbonate reagent is present in the inventive compositions at about 0.01% to about 5% by weight, at about 0.02% to about 3% by weight, or at about 0.02% to about 2.0% by weight, dependent on the product formulation and application. Preferably, the bicarbonate reagent (e.g., potassium bicarbonate) conforms to US Pharmaceutical grade manufacturing standards. Bicarbonate solutions and horticultural oils are natural substances with art-recognized antifungal properties, and are well suited for the biocompatible treatment of diseased plants. According to preferred aspects of the present invention, bicarbonate reagents synergize with the at least one essential oil, and/or soap and glycerin of the inventive compositions to provide surprisingly effective antifungal activity.

For example, powdery mildew, caused by *Sphaerotheca pannosa* (Wall ex. Fr.) Lerv. var. rosae Wor., is the most costly disease of glasshouse grown *Rosa* spp. in the world, together with blackspot, caused by Diplocarpon rosae Wolf, forming the most serious pair of diseases of nursery and garden grown roses. The minimum effective bicarbonate treatment necessary for the management of rose powdery mildew has been determined (R. K. Horst and H. W. Israel of Cornell University "Managing Fungal Diseases of Ornamentals with Bicarbonates and Determining Their Mode of Action"; Progress Report to the American Floral Endowment, Aug. 21, 1992). Horst and Israel developed four experimental near-optically ideal systems to find the time/space window in the rose powdery mildew cycle through which the mechanism(s) for bicarbonate's efficacy could be observed. The systems were developed in a way that permitted microscopic and quantitative determinations of (i) whether bicarbonates function as eradicants and/or preventives; (ii) whether, when, and what rate bicarbonates adversely impact spore viability, germinability, and/or penetrability; (iii) bicarbonate dose response levels; and (iv) adjuvant dose response levels. These studies showed that powdery mildew and/or blackspot are significantly managed by weekly sprays of 0.5% (w/w) aqueous solutions of either potassium or sodium bicarbonate 0.5% (or by 1.0% (v/v) SunSpray Ultra-fine Spray Oil). Recent studies on effective minimum dose indicate that although 0.5% and 0.25% concentrations of both sodium and potassium bicarbonate significantly reduce powdery mildew severity, 0.5% is the more effective dose. Horst and Israel's studies also show that ammonium bicarbonate is not as efficacious as sodium or potassium, and that 0.05% bicarbonate sprayed weekly will not effectively control powdery mildew. Mechanism studies were conducted by Horst and Israel with naturally inoculated leaflets sampled 24 and 48 hours after treatment in numerous ways which indicated noteworthy results with respect to conidial germination. These included striking differences in efficacy among the bicarbonates and their concentrations, greatly enhanced efficacies of bicarbonates over the organic fungicide Banner, and no effects at all on germination by SunSpray oil alone. Studies using intact plants revealed that after one adaxial foliar spray application of potassium bicarbonate (i) superficial pathogen structures are eradicated, (ii) host epidermal layers recover completely from infection but contain phenolic-rich cells, and (iii) the bicarbonate and/or its effect(s) are neither mediated nor translocated by the host tissues. Thus, the work by Horst and Israel indicates that bicarbonate either desiccates, plasmolyzes, ruptures, and/or devacuolates fungal pathogen cells, including pre-germinated spores. Any or all of these effects, although ontogenetically nonspecific, are presently thought to be markedly deleterious to the fungus.

According to particular aspects of the present invention, bicarbonate agents are particularly effective and synergize with the soaps, glycerin, and essential oil(s) of the inventive compositions, and such bicarbonate agents, when present in the inventive compositions (e.g., when present with an essential oil and/or a soap and glycerin), have substantial utility to provide fungal knock down. According to additional aspects, the bicarbonate reagents serve to buffer the inventive compositions, providing for a safer and less harsh product.

Alternatively, as is appreciated in the art, sulfur and copper based compounds are effective fungicidal agents, and may be used in the inventive compositions.

In particular aspects, the inventive compositions comprise a soap base (with retained glycerin) and essential oils (e.g., as insecticide and repellant), food oils (e.g., as a miticide), a bicarbonate reagent (e.g., USP potassium bicarbonate or sodium bicarbonate) (e.g., as fungicide) and water as diluent/ carrier. Such embodiments have surprising and substantial utility to address not one, but three critical needs for growers; namely, insects, mites and fungus. According to aspects of the present invention, the main components function together harmoniously, without impeding or altering the properties of any other component, and synergize to facilitate function of the other components. For example, the soap by itself acts as a contact killer, but has little if any effect as a miticide. The essential plant oils contain pesticidal properties and act as repellants. The food oils, in particular, act as a miticide by smothering the insect larvae thereby preventing hatching and by preventing breathing by adult insects. Bicarbonate reagents (e.g., potassium bicarbonate or baking soda) is not ineffective as a fungicide unless combined with oil as the carrier (Horst and Israel, supra). Thus, the essential oil (e.g., food oil) serves two purposes as both a miticide and the enabling carrier for the potassium bicarbonate or sodium bicarbonate (fungicide) or any other bicarbonate deemed useful for this purpose. Other wetting agents, carriers, adjuvants, etc., may be used in the art. Additionally, other organic or pure essential and food oils could be substituted to achieve the same or similar effect. Product formulations may vary, depending on the availability of particular ingredients.

It should be noted that certain prior art insecticidal soap products contain approximately 4% potassium salts of fatty acids carried in 96% ethyl alcohol. By dramatic contrast, particular embodiments of the present invention comprise from about 12 to about 17% of essential oil, (e.g., organic peppermint oil, and/or other organic or pure plant essential oils), about 8 to about 12% fatty acids of olive oils, and retained glycerin, together comprising about a 22 to about a 25% product content before dilution with a water carrier or diluent.

Therefore, particular aspects of the present invention provide novel pesticidal (insects, mites and fungus) compositions, comprising glycerin-based organic or pure saponified fatty acids (e.g., of olive and coconut oil (soap)), one or more organic or pure plant essential oils and/or derivatives thereof, natural or pure, as a contact pesticide. Additional aspects provide novel pesticidal compositions and methods for mechanically, physiologically and/or neurally controlling insects and mites. Further aspects provide novel safe, non-toxic pesticidal compositions and methods that will not harm mammals, pollute ground water, rivers or streams, or the environment. Yet further aspects provide novel pesticidal compositions and methods that have a pleasant scent or are unscented, and that can be applied without burdensome safety precautions of goggles, overalls and the like. Particular aspects provide novel pesticidal compositions and methods as described herein above, which can be inexpensively produced or employed. Particular aspects provide novel pesticidal compositions and methods to which pests cannot build immunity and/or resistance.

The above and other objects are accomplished by the present invention, which in particular aspects is directed to novel pesticidal compositions comprising organic or pure, glycerin based soap, plant essential oils and/or derivatives thereof, pure or organic food oils, in a mixture with suitable carriers. Additional aspects provide methods for controlling insects, mites and fungus by applying a pesticidally-effective amount of the above pesticidal compositions to the insects, plants or crops. In preferred aspects for controlling fungus, the invention utilizes the addition of a bicarbonate reagent (e.g., USP potassium bicarbonate or sodium bicarbonate or any other bicarbonate having fungicidal utility when combined with food oils).

It is to be understood that the foregoing general description is exemplary and explanatory, and should not be viewed as being restrictive of the invention. For example, in a preferred embodiment, the present invention is directed to a pesticidal composition for controlling insects, mites and fungus comprising organic or pure soap (as herein defined) plant essential oils selected from the group consisting of but not limited to peppermint, lavender, almond, cinnamon, geranium, rosemary, organic food oils including but not limited to canola, coconut, hemp and olive, and finally USP potassium bicarbonate or sodium bicarbonate or any other bicarbonate having fungicidal activity. It will be appreciated by the skilled artisan that the pesticidal compositions (e.g., comprising one or more US FDA approved plant essential oils) of the present invention unexpectedly exhibit excellent pesticidal activities, and can be used in lieu of conventional pesticides. Without being bound by mechanism, it is believed that plant essential oils antagonize a pest's nerve receptors or may act as Phase I and/or Phase II drug metabolizing enzyme inhibitors. Alternatively, plant essential oils may act via an alternative mode of action. The plant essential oils may act as agonists or antagonists against the octopamine receptors that are distinct to invertebrates. In any event, the net effect of the activities of the inventive synergistic compositions disclosed herein is heretofore unknown and unexpected.

Use of pesticidal compositions of the present invention generally results in substantial (e.g., 100%) mortality on contact, and provides significant repellant properties for extended periods of time. As such, they are advantageously employed as pesticidal agents for plants or crops.

The inventive compositions may be applied as a liquid, mist or aerosol, and may be applied directly to a pest, and/or to any surface (e.g., surfaces of plant parts, or other surfaces in communication with plants or pests) potentially contacted by the pest whereby the pest is in-turn contacted by the inventive composition. The inventive compositions may be in the form or concentrates, which are diluted prior to use, or may be in directly usable (no dilution necessary or recommended) forms. Concentrated will typically comprise a correspondingly higher concentration of the ingredients (e.g., the fatty acid soap base, the essential oil (and/or food oil), may be present at about 0.01% to about 70% by volume, glycerin may be present at 0.01% to about 20% by volume, and the bicarbonate agent at about 0.02% to about 20% by weight). Moreover, concentrates lacking one or more ingredients are within the scope of the present invention, and wherein optimal multi-functional compositions are produced by addition of a plurality of such concentrates. Those of ordinary skill in the art will be able to effectively use the inventive synergistic pesticidal formulations, and if necessary, will be able to make optimal dilutions, or select delivery systems to conform to particular needs and situations, without undue experimentation. Therefore, the foregoing is considered as illustrative of the principles of the invention, and numerous modifications and changes will readily occur to those skilled in the art, it is not desired or intended to limit the invention to the exemplary embodiments shown and described, and all suitable and effective modifications and equivalents may be employed, falling within the scope of the invention.

Alternate Soap Base Embodiments

In additional aspects, the inventive compositions comprise: a soap base (e.g., potassium salts of fatty acids; but not SLS), and/or glycerin (or any other safe soap base deemed suitable for the purpose); at least one essential oil (which may or may not be organic, pure or synthetic); a bicarbonate reagent, (e.g., USP potassium bicarbonate, or sodium bicarbonate or any other bicarbonate having utility for the present purposes); and water or other agent (e.g., alcohol) as diluent and/or carrier. In preferred embodiments, the soap base and essential oil(s) are 'organic' or "pure." In particular aspects, the components are blended and bottled by a certified organic food manufacturer under strict quality control. For example, the ingredients are blended in stainless steel tanks under the standards and guidelines of the USDA for Organic products.

Soap base. In particular aspects, the soap comprises an unsaturated fatty acid having 10 to 18 carbon atoms, 11 to 18 carbon atoms, or 12-18 carbon atoms, or the respective salt. Preferably, the unsaturated fatty acid has 12-18 carbon atoms. The fatty acid is preferably selected from oleic acid, linoleic acid, their soaps (salts), and mixtures thereof. Linoleic acid or ricinoleic acid may be present. The cation forming the salt or soap with the fatty acid is, for example, typically sodium, potassium or ammonium. In particular aspects, an unsaturated fatty acid having 10 to 18 carbon atoms, 11 to 18 carbon atoms, or 12-18 carbon atoms, or the respective salt, is used in a mixture with a small amount of a saturated fatty acid having about 12-18 carbon atoms. Particularly preferred is a mixture of the salts of oleic acid and linoleic acid. One of the most convenient mixtures of the salt comprises from about 50% to about 80% by weight of oleic acid and 40% to 5% by weight of linoleic acid, the balance being a small amount, for example, at most 20% by weight of, a saturated fatty acid (e.g., palmitic acid and/or stearic acid). SLS is not suitable as discussed in detail herein. Not only is SLS harmful to humans, but, as well-known in the art, it is harsh and harmful to plants, particularly when it forms deposits upon plant surfaces.

In particular aspects, the soap base is present in the inventive compositions at about 0.01% to about 40% by volume, at about 0.01% to about 30% by volume, at about 5% to about 25% by volume, at about 10% to about 20% by volume, at about 10% to about 25% by volume, at about 5% to about 20% by weight, or at about 10% to about 15% by weight.

Exogenous glycerin. Particular compositions comprise, in addition to a soap base and retained glycerin, about 0.01% to about 5% of exogenous glycerin. Preferably, exogenous glycerin is present in the compositions at about 0.5% to about 3%. Preferably, exogenous glycerin is present in the compositions at about 2.0%. According to aspects of the present invention, glycerin synergizes with other ingredients to enhance one or more pesticidal activities, and to provide for a better appearance on plant parts (e.g., for shiny leaves). Without being bound by mechanism, the glycerin serves to preclude deposition of, for example, fatty acid salts and/or bicarbonate salts (see below describing bicarbonate-containing embodiments). Fatty acid salts of prior art products can form deposits on plants, causing leaf burn and leaf fall (particularly over extended application periods), and may result in plant death. The present invention thus solves this art-recognized problem by providing glycerin, which serves to eliminate chalky residue, thereby eliminating leaf burn and leaf fall. Furthermore, glycerin absorbs the essential oil and traps its repellent properties to provide for extended protection from new infestations for several (e.g., up to four weeks) weeks, depending upon the conditions, thus further reducing pesticide use in the environment.

Essential oil(s). Particular inventive compositions comprise one or more essential oils (e.g., plant essential oils) as described herein above (e.g., peppermint, lavender and rosemary, etc.). In particular aspects, these essential oils comprise about 0.01% to about 40%, about 0.01% to about 30%, about 5% to about 25%, about 5% to about 20%, about 5% to about 15%, or about 1% to about 10% of the product by weight, depending on formulation, application and dilution.

Food oils. Particular inventive compositions comprise one or more food oils as describe herein above, and including but not limited to olive, canola, cottonseed, cinnamon, almond, coconut, hemp, etc. In particular aspects, these food oils comprise about 0.01% to about 40%, about 0.01% to about 30%, about 5% to about 25%, about 5% to about 20%, about 5% to about 15%, or about 1% to about 10% of the product by weight, depending on formulation, application and dilution.

Various oils have been used for centuries to control insect and mite pests. Without being bound by mechanism, oils have different effects on pest insects. The most important is that they block the air holes (spiracles) through which insects breathe, causing them to die from asphyxiation. In some cases, oils also may act as poisons, interacting with the fatty acids of the insect and interfering with normal metabolism. Oils also may disrupt how an insect feeds, a feature that is particularly important in the transmission of some plant viruses by aphids. Oils pose few risks to people or to most desirable species, including beneficial natural enemies of insect pests. This allows oils to integrate well with biological controls. Toxicity is minimal, at least compared to alternative pesticides, and oils quickly dissipate through evaporation, leaving little residue. Oils are also easy to apply with existing spray equipment and can be mixed with many other pesticides to extend their performance. Vegetable oils also can be used as insecticides, although the type of oil can greatly affect its activity, cottonseed oil is generally considered the most insecticidal of the vegetable oils. Soybean oil, the most commonly available vegetable oil used in cooking, also has substantial utility. Variations may include differences in viscosity or color dependent upon the method of extraction, and the conditions under which the oils were processed (with heat), as well as the origin of the plants, grains or seeds from which the oils are extracted.

Bicarbonate reagent. Particular inventive compositions comprise, as described in detail herein above, a bicarbonate reagent (e.g., potassium bicarbonate or sodium bicarbonate, or any other bicarbonate deemed useful for the purpose) at about 0.02% to about 10% by weight, dependent on product formulation and application.

Numerous variations of the soap base (soap/detergent/glycerine base) are contemplated, dependent upon the amount of diluent, colorants or fragrance that may be used during the mixing process. Preferably, as described herein above, the inventive compositions are liquids, and the variations are preferably limited by virtue of the base's liquid properties.

In particular aspects therefore, the inventive compositions comprise: a soap base (soap/detergent/glycerin); at least one essential oil (e.g., as insecticide and repellant); at least one food oil (e.g., as miticide) that may be the same or different as the essential oil; a bicarbonate reagent (e.g., potassium bicarbonate, sodium bicarbonate or other bicarbonates deemed useful for the purpose) (e.g., as fungicide and/or buffer); and a diluent or carrier, which may be, for example, water or alcohol.

According to preferred aspects, the components, as described herein above, function together harmoniously without impeding or altering the properties of any other component, and synergistically facilitate function of the other components. Without being bound by mechanism, the soap by itself acts as a contact killer, but has little if any effect as a miticide. The essential plant oils act as repellants, and certain of them may possess pesticidal properties. The food oils act as a miticide by blocking the air holes (spiracles) through which insects breathe, causing them to die from asphyxiation. In some cases, oils also may act as poisons, interacting with the fatty acids of the insect and interfering with normal metabolism. Oils also may disrupt insect feeding, a feature that is particularly important in the transmission of some plant viruses by aphids. Bicarbonates (e.g., potassium bicarbonate, sodium bicarbonate or other bicarbonates), as described in detail herein above, are highly effective as a fungicide but when combined with oil as the carrier. Thus, the food oil serves two purposes as both a miticide and the carrier that catalyzes, enhances or enables the fungicidal properties of the bicarbonate reagent (e.g., potassium bicarbonate, sodium bicarbonate or other bicarbonate deemed useful for the purpose). Other art-recognized wetting agents, carriers, adjuvants, etc., may be used. Additionally, other essential and food oils could be substituted to achieve the same or similar effect. Formulations may change, from time to time, depending on the availability of certain ingredients.

The inventive compositions may be applied as a liquid, mist or aerosol, and may be applied directly to a pest, and/or to any surface (e.g., surfaces of plant parts, or other surfaces in communication with plants or pests) potentially contacted by the pest whereby the pest is in-turn contacted by the inventive composition. The inventive compositions may be in the form or concentrates, which are diluted prior to use, or may be in directly usable (no dilution necessary or recommended) forms. Concentrated will typically comprise a correspondingly higher concentration of the ingredients (e.g., the fatty acid soap base, the essential oil (and/or food oil), may be present at about 0.01% to about 70% by volume, glycerin may be present at 0.01% to about 20% by volume, and the bicarbonate agent at about 0.02% to about 20% by weight). Moreover, concentrates lacking one or more ingredients are within the scope of the present invention, and wherein optimal multi-functional compositions are produced by addition of a plurality of such concentrates. Those of ordinary skill in the art will be able to effectively use the inventive synergistic pesticidal formulations, and if necessary, will be able to make optimal dilutions, or select delivery systems to conform to particular needs and situations, without undue experimentation.

Further Miticide/Fungicide Embodiments

Yet further aspects of the present invention provide novel multi-functional synergistic compositions having substantial utility for combined treatment of mites and fungus by application of a single composition.

Particular aspects provide a method for controlling mite and fungal pests with a single composition, comprising contacting at least one pest, or a surface or plant or portion thereof susceptible to the at least one pest, with a pesticidally effective amount of a composition comprising, along with an aqueous carrier or diluent: a non-petroleum-based food oil as defined herein; and a bicarbonate agent as defined herein, wherein controlling mite and fungal pests with a single composition is afforded. Preferably, the non-petroleum-based food oil is present at about 0.01% to about 40% by volume, at about 5% to about 10% by volume, or at about 1% to about 10% by volume. Preferably, the composition further comprises about 0.01% to about 5% by volume, or about 2.0% by volume of exogenous glycerin. Preferably, the bicarbonate agent comprises potassium bicarbonate present at about 0.02% to about 3% by weight, or at about 0.02% to about 2.0% by weight. Preferably, the non-petroleum-based food oil is present at about 0.01% to about 20% by weight, or at about 0.1% to about 10% by weight, and the bicarbonate agent comprises a bicarbonate salt present at about 0.02% to about 5.0% by weight, or at about 0.02% to about 2% by weight. Preferably, the non-petroleum based food oil is at least one selected from the group consisting of soybean, cottonseed and canola. Preferably, the food oil is organic.

The inventive compositions may be applied as a liquid, mist or aerosol, and may be applied directly to a pest, and/or to any surface (e.g., surfaces of plant parts, or other surfaces in communication with plants or pests) potentially contacted by the pest whereby the pest is in-turn contacted by the inventive composition. The inventive compositions may be in the form or concentrates, which are diluted prior to use, or may be in directly usable (no dilution necessary or recommended) forms. Concentrated will typically comprise a correspondingly higher concentration of the ingredients (e.g., the non-petroleum based food oil may be present at about 0.01% to about 90% by volume, glycerin may be present at 0.01% to about 20% by volume, and the bicarbonate agent at about 0.02% to about 20% by weight). Moreover, concentrates lacking one or more ingredients are within the scope of the present invention, and wherein optimal multi-functional compositions are produced by addition of a plurality of such concentrates. Those of ordinary skill in the art will be able to effectively use the inventive synergistic pesticidal formulations, and if necessary, will be able to make optimal dilutions, or select delivery systems to conform to particular needs and situations, without undue experimentation.

EXAMPLE 1

The Inventive Compositions were Shown by a Commercial Grower to be Surprisingly Effective for the Control of Powdery Mildew on Rose Plants A large efficacy study was conducted in collaboration with Greenheart™ Farms (Arroyo Grande, Calif.). The study was coordinated by Mr. Bill De Vor, production manager/grower of roses. Greenheart™ Farms is an art-recognized, well-known grower of quality live floral plants (e.g., poinsettias, roses, etc.), and comprises broad knowledge of products for vegetable, herb and flower farming, reclamation projects, live potted flowers for end consumers, and container stock for farming and/or landscaping applications. Greenheart™ Farms has well-established performance parameters and maintains frequently tested "pulse-points" to monitor compliance specification and strictly adhere to phytosanitary conditions.

Materials. Rose Pharm™ was used to control pests (e.g., powdery mildew) in the context of rose growing for a period of about year. Rose Pharm™ is an exemplary inventive composition comprising about 7% soap with retained glycerin (from oleic acid/potassium hydroxide), about 2% exogenous glycerin, about 2.0% peppermint oil, about 0.1% Rosemary Oil, about 1.5%, Cottonseed oil, (or Soybean oil), about 1.5% Non GMO Canola Oil, about 0.5% potassium bicarbonate, about 1.0% Vitamin E (as preservative).

Results. Bill DeVor, Senior Rose Grower at Greenheart™ Farms, conducted efficacy tests for the treatment and control of insect infestations (e.g., aphids, whiteflies etc.) and fungal infections (e.g., powdery mildews) at the Greenheart Farm facility in an effort to find a non-toxic solution to heavy chemicals. Weekly application of Rose Pharm™ was reported by Greenheart™ Farms to be surprisingly effective at controlling powdery mildew on rose plants. The product left plants healthier and shinier than expected (compared to conventional products). The plants continued to be disease resistant after only one or two product applications. The efficacy was sufficient such that continued applications could be spaced over multiple weeks, and a more diluted (e.g., up to 70% less product) form.

Greenheart™ Farms, based on this study and the surprising effectiveness relative to conventional products, has elected to use Rose Pharm™ as its preferred product for this purpose. The success of these tests at Greenheart™ Farms has led to the use of this invention as an ongoing pest management strategy at Greenheart. Furthermore, Greenheart™ Farms now offers the products to their customers through catalog sales.

The invention claimed is:

1. A composition of matter, comprising a biologically effective amount of a combination of,
   about 5% by weight to about 8% by weight soap,
   an effective amount of glycerin,
   about 1% by weight to about 5% by weight of an essential oil, comprising oil of rosemary and at least one of oil of peppermint, or oil of cinnamon, or oil of almond, and
   about 1% by weight to about 10% by weight food oil,
said composition of matter being effective to control fungus, insects and mites, wile not being toxic to host plant.

2. A composition as in claim 1 wherein said essential oil comprises oil of rosemary in combination with oil of peppermint.

3. A composition as in claim 1 wherein said essential oil comprises oil of rosemary in combination with oil of cinnamon.

4. A composition as in claim 1 wherein said essential oil comprises oil of rosemary in combination with oil of almond.

5. A composition as in claim 1, further comprising 0.25% by weight to 2% by weight bicarbonate salt.

6. A composition as in claim 1 comprising
   about 7% by weight of said soap,
   further comprising about 0.25% to about 0.5% by weight bicarbonate salt.

7. A composition of matter, consisting essentially of a biologically effective amount of a combination of
   about 5% by weight to about 8% by weight soap,
   an effective amount of glycerin,
   about 1% by weight to about 5% by weight of essential oil, comprising oil of rosemary and at least one of oil of peppermint, or oil of cinnamon, or oil of almond,
   about 1% by weight to about 10% by weight food oil, and
   a diluent liquid carrier,
said composition of matter being effective to control fungus, insects and mites, while not being toxic to host plants.

8. A composition as in claim 7 wherein said essential oil comprises oil of rosemary in combination with oil of peppermint.

9. A composition as in claim 7 wherein said essential oil comprises oil of rosemary in combination with oil of cinnamon.

10. A composition as in claim 7 wherein said essential oil comprises oil of rosemary in combination with oil of almond.

11. A composition as in claim 7, further including 0.25% to 2% by weight bicarbonate salt.

12. A composition of matter, comprising a biologically effective amount of a combination of
    about 5% by weight to about 8% by weight soap,
    an effective amount of glycerin,
    about 1% by weight to about 5% by weight essential oil,
    about 1% by weight to about 10% by weight non-saponified food oil, and
    about 0.25% to about 2% bicarbonate salt,
said composition being effective to control insects, mites, and fungus, while not being toxic to host plants.

13. A composition as in claim 12 wherein said essential oil comprises oil of rosemary in combination with oil of peppermint.

14. A composition as in claim 12 wherein said essential oil comprises oil of rosemary in combination with oil of cinnamon.

15. A composition as in claim 12 wherein said essential oil comprises oil of rosemary in combination with oil of almond.

16. A composition as in claim 12, comprising about 0.25 to about 0.5% by weight of said bicarbonate salt.

17. A composition of matter, comprising a biologically effective amount of a combination of
    about 14 parts by weight soap,
    about 4 parts by weight to about 6 parts by weight of one or more essential oils,
    an effective amount of glycerin,
    about 4 parts by weight to about 6 parts by weight non-saponified food oil, and
    about 0.5 part by weight to about 1 part by weight bicarbonate salt, and
    enough diluent carrier to maintain the composition in a liquid state,
said composition being a concentrate which, when further diluted, is effective to control insects, mites, and fungus, while not being toxic to host plants.

18. A composition as in claim 17 wherein said essential oil comprises oil of rosemary in combination with oil of peppermint.

19. A composition as in claim 17 wherein said essential oil comprises oil of rosemary in combination with oil of cinnamon.

20. A composition as in claim 17 wherein said essential oil comprises oil of rosemary in combination with oil of almond.

21. A composition as in claim 17, comprising about 1 part by weight of said bicarbonate salt.

* * * * *